United States Patent [19]

Hansen

[11] 3,960,950

[45] June 1, 1976

[54] PROCESS FOR CARBODIIOMIDE SYNTHESIS

[75] Inventor: Robert L. Hansen, Roseville, Minn.

[73] Assignee: Minnesota Mining and Manufacturing Company, St. Paul, Minn.

[22] Filed: Sept. 9, 1974

[21] Appl. No.: 504,296

Related U.S. Application Data

[62] Division of Ser. No. 368,355, June 8, 1973, Pat. No. 3,862,989.

[52] U.S. Cl............................................. 260/566 R
[51] Int. Cl.$^2$....................................... C07C 119/04

[58] Field of Search .................. 260/566 R, 551 CD

[56] References Cited
UNITED STATES PATENTS 3,152,131   10/1964   Heberling, Jr............ 260/551 CD X

*Primary Examiner*—Gerald A. Schwartz
*Attorney, Agent, or Firm*—Alexander, Sell, Steldt & Delahunt

[57] ABSTRACT

Phosphine oxides are prepared from terpenes and are found to be valuable as catalysts in the condensation of isocyanates to yield carbodiimides.

3 Claims, No Drawings

PROCESS FOR CARBODIIOMIDE SYNTHESIS

This is a division of application Ser. No. 368,355 filed June 8, 1973, now U.S. Pat. No. 3,862,989.

This invention relates to the preparation of terpene phosphine oxides and particularly to production of phosphine oxides from camphene and to the product camphene phosphine oxides. More particularly, it relates to alkyl or aryl substituted phosphine oxides. It further relates to the process for producing carbodiimides from isocyanates using terpene phosphine oxides and particularly camphene alkyl or aryl substituted phosphine oxides.

Carbodiimides are relatively well-known compounds corresponding to the general structure $$R'''(N=C=NR'')_nN=C=NR'$$

where $n$ is an integer from 0 to a large number, preferably not over about 20. R' and R''' may be the same or different, substituted or unsubstituted monovalent organic radicals free from isocyanate reactive hydrogen atoms and R'' is a olyvalent, generally divalent, organic radical free from isocyanate reactive hydrogen atoms. Although R'' may be, for example, trivalent to provide a branch which may be free of or may contain carbodiimide groups, a divalent group is preferred when soluble or thermoplastic materials are desired. When R'' is polyvalent, branched or cross-linked polycarbodiimides result. Different R'' groups may be used together to give slight branching in order to modify properties. Any or all of the groups R, R'' or R' may contain fluoroaliphatic radicals to provide oil and water repellent characteristics and to minimize solubility in common solvents. The carbodiimides have many known uses, such as molding powders, coatings, films, and treating compositions for a variety of substrates. In general, carbodiimides are prepared by the reaction of mono-, di- or poly-isocyanates in the presence of suitable catalysts so that the isocyanate groups condense with the liberation of carbon dioxide to form the carbodiimide linkages. In general, it is preferred that carbodiimides include at least 1% and preferably 10% or more of —N=C=N— groups. Because of the wide variety of reactions that isocyanate groups can undergo, selection of a suitable catalyst is an important factor in preparing carbodiimides.

One class of suitable catalysts is the phosphacyclopentyl derivatives, as prepared in U.S. Pat. Nos. 2,663,737, 2,663,738, and 2,663,739. The use of these materials as catalysts for carbodiimide formation is described in U.S. Pat. No. 2,853,518 and especially in U.S. Pat. No. 2,853,473. These materials are, in many cases quite effective as catalysts for the desired condensation reaction, but their preparation requires extended times and yields are frequently low. This class of phosphorus compounds are included in terms phospholine, phospholine oxide, phospholine sulfide, phospholidines and the oxides and sulfides thereof.

Another class of phosphorus-containing compounds which has been described as useful as catalysts for the carbodiimide reaction are phosphetane oxides, in which the quinquevalent phosphorus bearing an alkyl, aryl or alkyl group and an oxide oxygen is a member of a four-membered ring, the other three being methylene or alkyl substituted methylene groups, as described in British Patent 1, 215, 157. The Phosphetane oxides are generally prepared by condensation of a substituted dichlorophosphine with a noncyclic aliphatic olefin bearing a tertiary carbon atom beta to the oelfinic carbon atom in the presence of a Friedel-Crafts catalyst such as aluminum chloride, followed by hydroylsis. Such a structure in skeletal form is

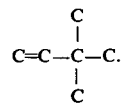

The method of preparation is convenient, but the required noncyclic olefins are relatively expensive or inaccessible.

It is an object of this invention to provide a novel catalyst for the condensation of isocyanates and for polyisocyanates to carbodiimides and particularly compounds containing the carbodiimide linkage. Another object of the invention is to provide a new process for the production of polycarbodiimides. A further object of the invention is to provide a process for the production of phosphine oxides and particularly a process which is adapted to the use of readily available materials. Other objects will become evident hereinafter.

In accordance with these and other objects of the invention, a new class of phosphine oxides has now been discovered which can be prepared conveniently from inexpensive, readily available raw materials and which provides effective catalysis for the condensation of mono or polyisocyanates to carbodiimides. In these compounds the phosphorus atom is believed to be a member of a ring consisting additionally of three carbon atoms, i.e., a phosphetane oxide, but at least part of the annular carbon atoms are themselves part of a polynuclear alicyclic structure. A preferred class of these materials is those having the formula $C_{10}H_{16}PRO$, wherein R is alkyl, aryl or aralkyl, of up to about 10 carbon atoms, substituted on the phosphorus atom. Particularly preferred is phenyl. They are conveniently prepared by reaction in the presence of a Friedel-Crafts catalyst of a substituted dihalophosphine, e.g., $RPCl_2$, particularly phenyl dichlorophosphine, and a bicyclic terpene of the class of camphene, alpha and beta pinene, and sabinene. The preferred starting material is camphene.

Suitable dihalophosphines include particularly dichlorophosphines having alkyl or aryl group attached directly to phosphorus. In particular, alkyl group of 1 to about 10 carbon atoms and aryl groups such as phenyl, tolyl, xylyl and the like of about 6 to 10 carbon atoms and preferably phenyl. The alkyl or aryl groups may be substituted by compatible groups which are unreactive with aluminum chloride or isocyanate groups under reaction conditions and are free from non aromatic unsaturation. Preferably, the alkyl and aryl groups are unsubstituted.

The reaction is suitably carried out by forming a complex between a Friedel-Crafts catalyst such as anhydrous aluminum chloride or ferric chloride and the substituted dihalophosphine, conveniently in the presence of inert solvents such s methylene chloride, or nitrobenzene. This complex is then reacted with the bicyclic $C_{10}H_{16}$ terpene at a temperature between −25° and 100°C., conveniently at a temperature of about 15°–30°C. The product may be used as a catalyst in the solvent as formed, as recovered by evaporation of the solvent, or in a more purified form, for example, that derived by vacuum fractionation of the reaction mixture.

The desired carbodiimides are obtained by treating an organic isocyanate, or mixture of organic isocyanates, including polyisocyanates, with a catalytic amount of the order of 0.5 to 2.5%, preferably about 1–1.5% of the weight of isocyanates of the phosphine oxide.

When using an organic monoisocyanate, such as phenylisocyanate, to prepare an organic carbodiimide, the process using catalysts of the invention of the present invention may be illustrated as follows:

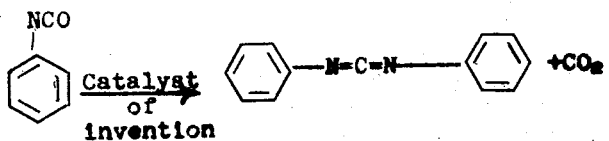

Representative organic monoisocyanates which may be used include methylisocyanate, ethylisocyanate, butylisocyanate, octylisocyanate, octadecylisocyanate, allylisocyanate, vinylisocyanate, pentylisocyanate, phenyleisocyanate, o-tolueneisocyanate, p-tolueneisocyanate, O-nitrophenylisocyanate, p-chlorophenylisocyanate, p-methoxyphenylisocyanate, p-biphenylylisocyanate, cyclohexylisocyanate, and decahydronaphthyl-isocyanate. It is to be understood that mixtures of these monoisocyanates may be used to form unsymmetrical or mixed carbodiimides.

The process of the present invention may also be carried out by using a polyisocyanate, such as a di- or tri-isocyanate. When using an organic diisocyanate, according to the process of the present invention, a condensation polymer having repeating carbodiimide linkages is prepared which may be of a high molecular weight and is substantially linear. The use of an organic diisocyanate alone may be illustrated as follows:

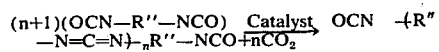

wherein R'' is a bivalent organic radical and $n$ is 1 or more. Organic diisocyanates which may be used in the process of the present invention include 2,4-tolylene diisocyanate, m-phenylene diisocyanate, 4-chloro-1,3-phenylene diisocyanate, 4,4'-biphenylene diisocyanate, 1,5-naphthylene diisocyanate, tetramethylene diisocyanate, hexamethylene diisocyanate, decamethylene diisocyanate, 1,4-cyclohexylene diisocyanate, 4,4-methylenedicyclohexylene diisocyanate, and 1,5-tetrahydronaphthylene diisocyanate. Mixtures of two or more of these organic diisocyanates may be used in which case the bivalent organic radical R'' in the above formula will not be the same in each recurring unit. It is further contemplated to employ mixtures of monoisocyanates and polyisocyanates, preferably in proportions or in sequential operations such that the monoisocyanates will provide caps or terminal groups. It is also to be understood that isocyanate-terminated polymers may be used in the process of the present invention so as to prepare substantially linear polymers containing a plurality of intralinear carbodiimide linkages. Representative isocyanate-terminated polymers which may be used include the reaction products of a polymer having terminal hydroxyl, amino, or carboxyl groups with a molar excess of an organic diisocyanate so as to provide an isocyanate-terminated polymers.

Here again it is to be understood that mixtures of two or more different isocyanate-terminated polymers may be used in the process of the present invention, in which case the bivalent organic radical R'' in the above formula will not be the same in each recurring unit. It is readily apparent that any of a wide variety of isocyanate-terminated polymers may be used in the process of the present invention.

Although aliphatic isocyanates provide useful carbodiimides, e.g. hexamethylene diisocyanate, aromatic isocyanates and diisocyanates such as tolylene diisocyanate are preferred because they react more rapidly to form carbodiimides. When substantial quantities of a tri(or higher) isocyanate are present in the reaction mixture, the resulting polycarbodiimide tends to be crosslinked, therefore infusible and insoluble. When small amounts of tri(or higher) isocyanate are present, a branched polycarbodiimide can be prepared which is soluble and fusible, generally having the same characteristics as the linear carbodiimides produced from mono and diisocyanates. Representative compounds containing more than two free isocyanate groups which may be used in amounts up to one molecule per molecule of product carbodiimide include 2,4,6-triisocyanatotoluene, p-isocyanatophenyl 2,4-diisocyanathophenyl ether, and compounds which are prepared from trifunctional reactants, such as the reaction product of 1 mol of castor oil with 3 mols of a diisocyanate, so as to obtain a compound having three free isocyanate groups. It is readily apparent that any of a wide variety of organic compounds containing more than two free isocyanate groups may be used in the process of the present invention.

A particularly useful substituent on the isocyanate component is a fluoroaliphatic radical. The fluoroaliphatic radical is preferably a fluorinated, saturated monvalent nonaromatic radical of at least three carbon atoms and generally less than about 20 carbon atoms. The aliphatic chain may be straight, branched, or if sufficiently large, cyclic, and may include catenary oxygen or trivalent nitrogen atoms bonded only to carbon atoms. Such hetero atoms are essentially inert. A fully fluorinated radical is preferred, but hydrogen or chlorine atoms may be present for two carbon atoms and preferably the radical contains at least one terminal perfluoromethyl group. Completely fluorinated aliphatic radicals containing about 5–12 carbon atoms are most preferred. The fluoroaliphatic radical may be appended to a diisocyanate such as

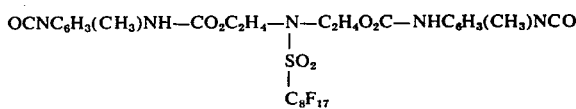

or part of a monoisocyanate such as $C_8F_{17}SO_2N(C_2H_5)C_2H_4O_2CNHC_6H_3(CH_3)NCO$ in which case the fluoroaliphatic radical forms a part of the terminal group of the product carbodiimide. Such fluoroaliphatic radical substituted carbodiimides suitably contain from about 5 to 45 percent by weight of carbon-bonded fluorine in the form of fluoroaliphatic radicals and are useful for the preparation of surface finishes to confer oil and water repellency and stain resistance, for example, to fabrics, especially fabrics consisting of snythetic fibers.

The invention is now more particularly illustrated by examples showing the production of a camphene phosphine oxide and the use thereof in preparing a carbodiimide.

EXAMPLE I

To a one liter round bottom flask fitted with stirrer, thermometer and funnel is added a slurry of 66.5 grams of aluminum chloride in 350 grams of $CH_2Cl_2$, and to this is added 89.5 grams of phenyl dichlorophosphine. Other alkyl and aryl dichlorophosphines are employed similarly. The flask is placed in a cooling bath to maintain the temperature of the contents at 20°–25°C. A solution of 68 grams of camphene in 150 grams of methylene chloride is added to it slowly with stirring. Stirring is continued for one hour after addition is completed, and the solution is then carefully poured, with stirring, into 750 ml. of an ice-water slurry. The lower methylene chloride layer is drawn off, washed first with an equal volume of 5% aqueous sodium bicarbonate, then with a saturated sodium chloride solution, and is finally dried over molecular sieve. Removal of solvent under reduced pressure at 35°C. leaves a residual viscous oil which is further purified by distillation at 0.5 torr and 180°–190°C. to give a colorless, viscous syrupy material. The product is shown by vapor phase chromatography to contain about 97% of a single component, $C_{10}H_{16}POC_6H_5$, designated camphene phenylphosphine oxide. The molecular weight by mass spectroscopy agrees with the empirical formula. The solution, the residual oil and the distillate are each effective catalysts for the formation of carbodiimides from isocyanates. The structure of the camhene phenyl phosphine oxide is not certain because of the possibility of rearrangements in the terpene structure as well as the probability of geometrical isomers.

EXAMPLE II

In a three liter glass flask equipped for distillation cooling and stirring is placed 77.2 grams of $C_8F_{17}SO_2N(C_2H_5)C_2H_4OH$ dissolved in 174.0 grams of methyl isobutyl ketone. The solution is dried by distillation of 50 grams of the ketone and then is cooled to 90°C. and 72.7 grams of 2,4-tolylene kiisocyanate is added. The vapor space is filled with nitrogen gas to a slight positive pressure and the reaction mixture is heated at 125°C. with stirring for one hour. The flask and contents are cooled to about 30°C. and 6.0 grams of the 25% solution of camphene phenyl phosphine oxide in methylene chloride, prepared in Examle I is added. The flask is heated to 115°C. and maintained there, with stirring for three hours, or until infra-red analysis confirms a substantially complete conversion of isocyanate to carbodiimide. The product can be used directly to solvent-treat fabrics to provide an oil and water repellent, stain resistant treatment, or the material may be converted e.g. to an aqueous emulsion, with or without additional polymeric material, for the treating solution.

EXAMPLE III

The procedure of Example I is repeated using beta pinene and a solution of beta pinene phenyl phosphine oxide in methylene chloride is obtained. The material is rather high boiling. A portion of the solution is employed at 25% concentration as was the phosphine oxide in Example II to catalyze formation of carbodiimide. Similar results are obtained and the resultant carbodiimide is employed in the treatment of fabrics with satisfactory results.

EXAMPLE IV

When other alkyl and aryl dihalophosphines are used in the procedures of Example I and III, other terpene alkyl and aryl phosphine oxides are obtained which are also useful as catalyst for the production of carbodiimides using the procedure of Example II or with other mono- or polyisocyanates.

What is claimed is:

1. In the process for the formation of organic carbodiimides from organic mono- or di-isocyanates or mixtures thereof with each other or with up to one organic tri-isocyanate per average molecule of organic carbodiimide formed, said organic mono-, di- and tri-isocyanates having no active hydrogen-containing substituents which are reactive with isocyanate groups, the step comprising treating each 100 parts by weight of said organic isocyanates with from about 0.01 to 10.0 parts by weight of bicyclic terpene alkyl or hydrocarbyl aryl phosphine oxide wherein alkyl is of 1 to 10 carbon atoms and hydrocarbyl aryl is of 6 to 10 carbon atoms.

2. The process of claim 1 wherein camphene alkyl or hydrocarbyl aryl phosphine oxide is used.

3. The process according to claim 1 wherein beta pinene phenyl phosphine oxide is used.

* * * * *